US00PP33416P2

(12) United States Plant Patent
Hardy

(10) Patent No.: US PP33,416 P2
(45) Date of Patent: Aug. 31, 2021

(54) ***ANEMONE* PLANT NAMED 'FP007'**

(50) Latin Name: *Anemone hybrida*
Varietal Denomination: FP007

(71) Applicant: Rosemary Hardy, Whitchurch (GB)

(72) Inventor: Rosemary Hardy, Whitchurch (GB)

( * ) Notice: Subject to any disclaimer, the term of this patent is extended or adjusted under 35 U.S.C. 154(b) by 0 days.

(21) Appl. No.: 17/131,059

(22) Filed: Dec. 22, 2020

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72; A01H 5/02
See application file for complete search history.

*Primary Examiner* — Keith O. Robinson
(74) *Attorney, Agent, or Firm* — Cassandra Bright

(57) ABSTRACT

A distinct new cultivar of *Anemone* plant named 'FP007', characterized by a long flowering season, double flowers with abundant tepals. Tepals are white with strong violet flushing on the underside. The new cultivar is an *Anemone* typically suited for ornamental container and landscape use.

3 Drawing Sheets

Latin name of the genus and species: *Anemone hybrida*. Variety denomination: 'FP007'.

BACKGROUND OF THE INVENTION

The new *Anemone* is the product of chance discovery by the inventor, Rosemary Hardy, in a home garden. The parent is *Anemone* 'MACANE007', U.S. Plant Pat. No. 27,383. The discovery and selection were made in October 2015 at the inventor's home garden in Whitchurch, England.

Asexual reproduction was performed by the inventor in February of 2017, by root cuttings at the breeder's home in Whitchurch, England. Subsequent asexual reproduction has proved the variety to be stable and reproduced true to type in successive generations.

SUMMARY OF THE INVENTION

The cultivar 'FP007' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FP007'. These characteristics in combination distinguish 'FP007' as a new and distinct *Anemone* cultivar:

1. Continuous flowering season from Mid June until Fall.
2. Double flowers with more tepals than comparable commercial *Anemone* varieties.
3. Broad flower buds.
4. Large foliage.

PARENTAL COMPARISON

Plants of the new cultivar 'FP007' are similar to the parent in most horticultural characteristics. However, plants of 'FP007' differ in the following:

1. Flowers of the new variety produce more tepals than the parent variety. Typically plants of 'FP007' produce an average of 45 tepals, 'MACANE007 typically produces 7 tepals.
2. The new variety has more violet coloration on the underside of the tepals.
3. Flower size of the new variety is typically 7.5 cm in diameter, flower diameter of 'MACANE007' is 5.8 cm.

COMMERCIAL COMPARISON

Plants of the new cultivar 'FP007' are similar to the known commercial variety *Anemone* 'MACANE004', U.S. Plant Pat. No. 27,384, in most horticultural characteristics. However, plants of 'FP007' differ in the following:

1. The flower bud is wider in 'FP007' compared to 'MACANE004'.
2. 'FP007' typically produces 45 tepals, compared to 7 in 'MACANE004'.
3. The flower is more heavily tinged lilac on lower tepal surfaces in 'FP007' than in 'MACANE004'.

Plants of the new cultivar 'FP007' are similar to the known commercial variety, *Anemone* 'Macane001' U.S. Plant Pat. No. 23,132 in some horticultural characteristics. However, plants of 'FP007' differ in the following:

1. 'FP007' typically produces 45 tepals, compared to 5 in 'MACANE001'.
2. Flower bud shape of 'MACANE001' is more ovate, flower bud shape of 'FP007' is more globular.
3. Foliage of 'MACANE001' is smaller than foliage of 'FP007'.
4. Flower form of 'FP007; is double, flower form of 'MACANE001' is single.

BRIEF DESCRIPTION OF THE PHOTOGRAPHS

The accompanying photograph in FIG. 1 illustrates in full color a typical plants of 'FP007' grown outdoors in a garden in Kirkcudbright, Scotland. This plant is approximately 15 months old.

Figure 1:
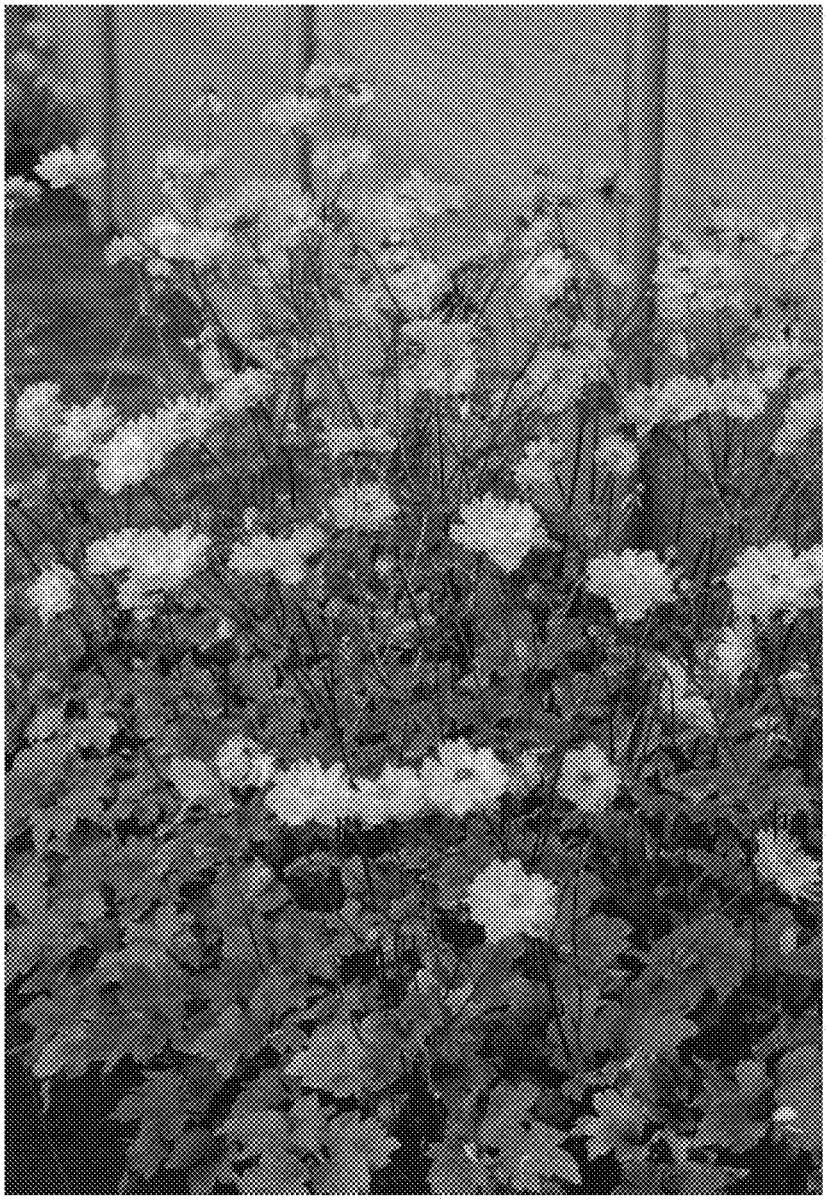
Figure 2:
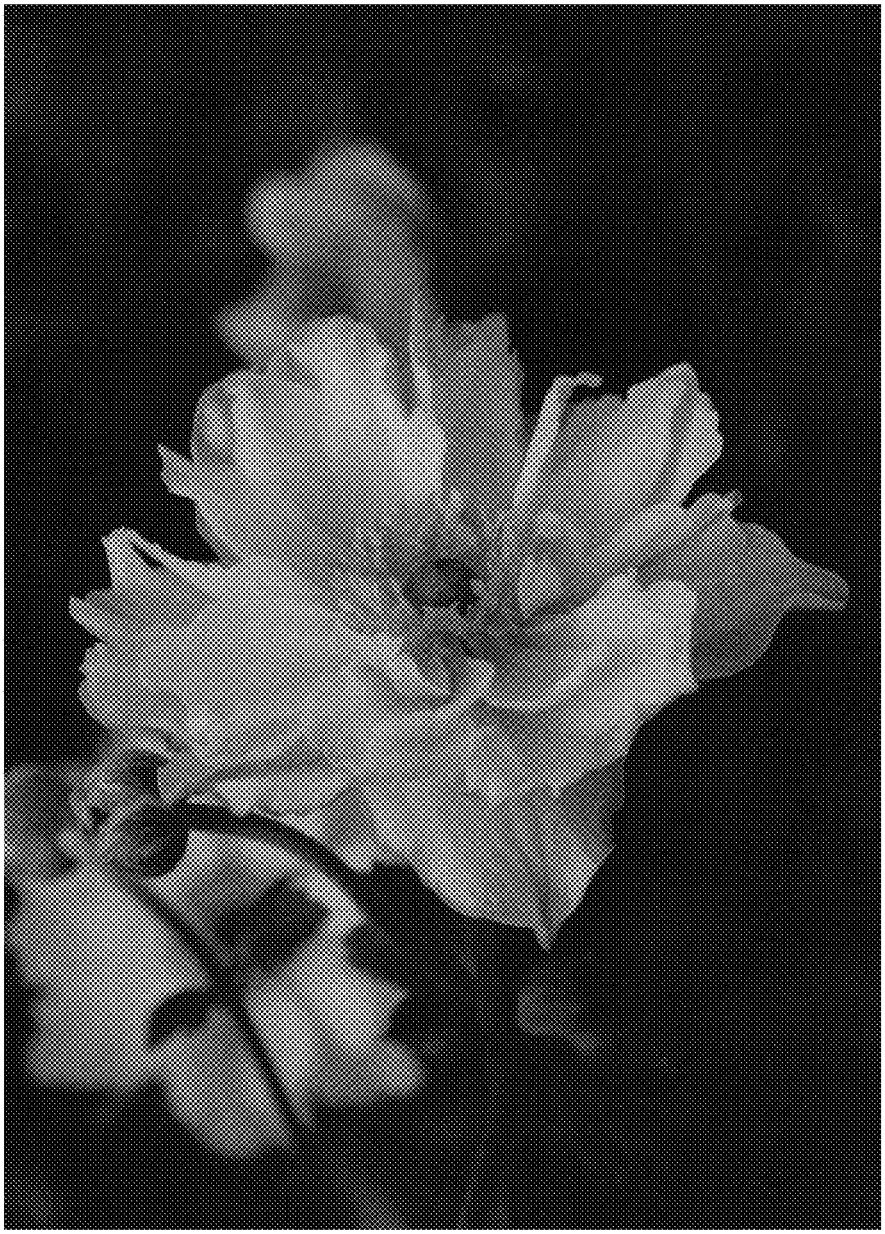
FIG. 2 illustrates a close up of the flower.
Figure 3:
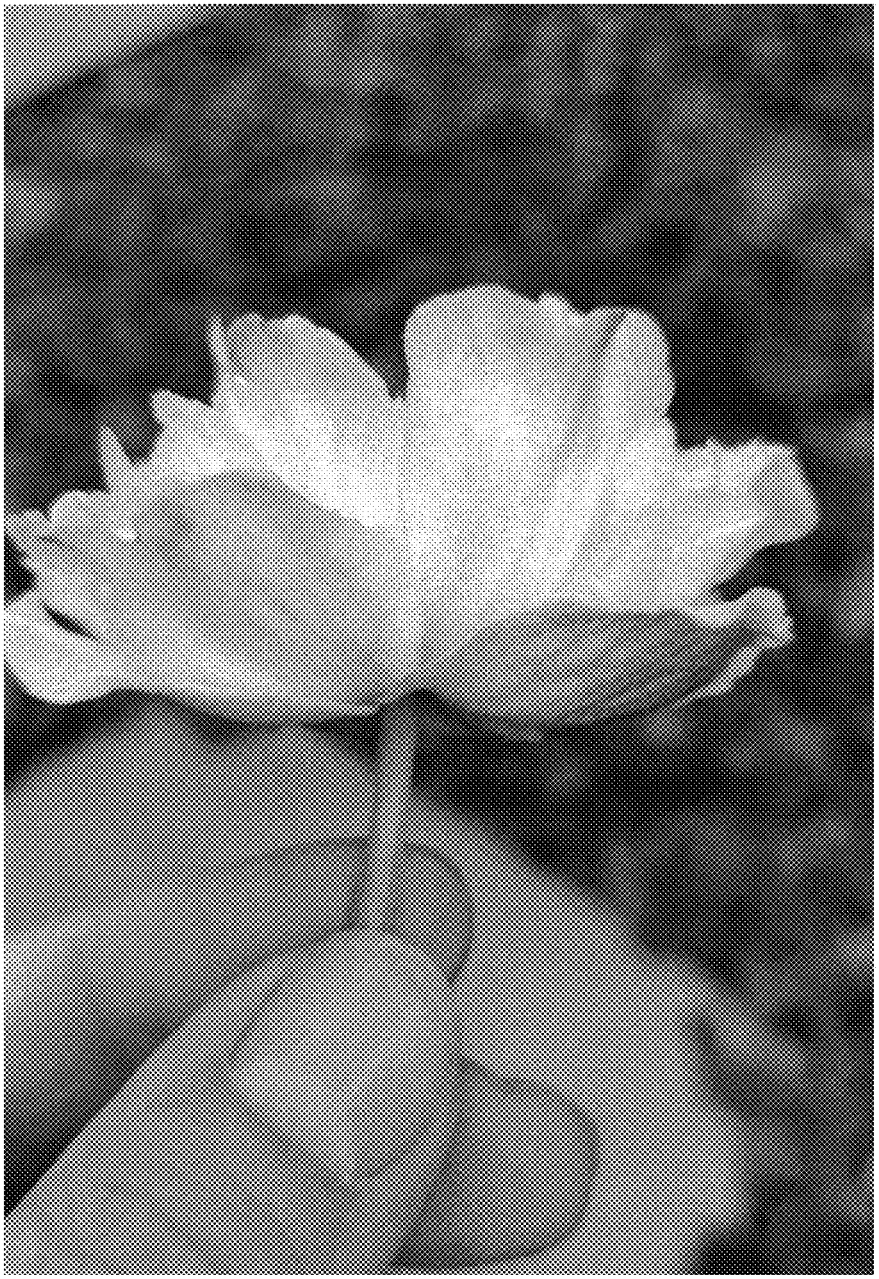
FIG. 3 illustrates the underside of the flower tepals.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'FP007' plants grown outdoors in High Hurstwood, United Kingdom. Measurements and numerical values represent averages of typical flowering types.

Botanical classification: *Anemone hybrida* 'FP007'.

Age of the plant described: Approximately 18 months from a division.

Container size of the plant described: 3 liter commercial container.

PROPAGATION

Time to produce a flowering plant from root-cutting: Nine to twelve months.

Root description: Fibrous, reddish-brown (not R.H.S. identified) in color.

Rooting habit: Dense, freely branching.

PLANT

Growth habit: Upright.

Pot size of plant described: 3 liter circular pot (19 cm).

Height: 85 cm.

Plant spread: 45 cm.

Growth rate: Moderate.

Branching characteristics: No lateral branches, flowering stems grow from a basal rosette.

Length of primary lateral branches: No lateral branches present, basal branching.

FOLIAGE

Leaf:

*Arrangement*.—Basal rosette.

*Leaves*.—

Shape: Trifoliate, broad ovate in outline.

Quantity: Approximately 6 to 8 per basal rosette.

Average Length: 19 cm.

Average Width: 17 cm.

*Individual leaflet blades*.—

Shape of blade: Ovate.

Apex: Short apiculate.

Base: Acute to short attenuate.

Margin: Biserrate.

Texture of top surface: Very slightly glossy.

Pubescence: Upper side sparsely covered with short adpressed hairs,

Aspect: Leaf blades in an average angle of 75° to petiole.

Color:

Young foliage upper side: Near RHS Green 143B.

Young foliage under side: Near RHS Green 143C.

Mature foliage upper side: Near RHS Green 137B.

Mature foliage under side: Between RHS Yellow-Green 147C.

Venation:

Type: Pinnate.

Venation color upper side: Near RHS Green 143A.

Venation color under side: Near RHS Yellow-Green 144B.

Petiole:

Length: 19 cm.

Diameter 0.3 cm.

Color: Near RHS Yellow-Green 146B, tinted Greyed-Purple 187B and 187C at the base.

Texture: Densely covered with short hairs.

Stipule Description (if present):

Length: 1.8 cm.

Diameter: 0.5 cm.

Color: Near RHS 145C.

Texture: Densely covered with short hairs.

FLOWER

Natural flowering season: July to September.

Days to flowering from rooted cutting: 9-12 months.

Inflorescence and flower type and habit: Inflorescence a terminal corymb, individual flowers rotate, double.

Rate of flower opening: 14 to 21 days from bud to fully opened flower.

Flower longevity on plant: Approximately one week.

Persistent or Self-Cleaning: Self-cleaning.

Bud:

*Shape*.—Broad ovate.

*Length*.—1.1 cm.

*Diameter*.—1.1 cm.

*Color*.—Near RHS Yellow-Green 147D.

Flower size:

*Diameter*.—7.5 cm.

*Depth*.—3.8 cm.

*Aspect*.—Outward to slightly nodding.

Tepals: No separate petals and sepals present, these floral structures are referred to as "Tepals" here.

*Quantity*.—45.

*Arrangement*.—Double or multi-whorled.

*Length*.—3.6 cm.

*Width*.—3.0 cm.

*Shape*.—Broad elliptic to slightly obovate.

*Apex*.—Obtuse to broad acute.

*Base*.—Broad cuneate.

*Margin*.—Entire. Undulate near apex.

*Texture, upper and lower surfaces*.—Glabrous, matte, slightly velvety.

*Color*.—When opening, upper surface: Near RHS N155C. When opening, lower surface: Near RHS Yellow-Green 145C at base. White N155B heavily tinged Purple-Violet N82C. moderately tinged Violet 85C. Fully opened, upper surface: Near RHS NN155A at base, NN155C at apex. Fully opened, lower surface: RHS NN155C, slightly tinged 145D on outer tepals. All tepals tinged Violet 84A and Purple-Violet N82C, outer tepals heavily tinged, amount of tinge diminishing towards the center of the flower and increasingly only in the center and apex of the tepal. The amount of violet tinge also further diminishes as the flowers age.

Bracts (if present): No bracts present.

Peduncles:

*Length*.—14 to 19 cm.

*Diameter*.—0.3 cm.

*Angle*.—Near vertical.

*Strength*.—Strong.
*Texture*.—Matte, densely covered with short soft hairs.
*Color*.—Near RHS Yellow-Green 145A, flushed Greyed-Purple 187C.

Fragrance: No fragrance.

REPRODUCTIVE ORGANS

Stamens:
*Number*.—Average range 150 to 200.

Anthers:
*Shape*.—Oblong.
*Length*.—Approximately 0.2 cm.
*Color*.—Near RHS Yellow-Orange 14A.
*Pollen*.—Color: Near RHS Yellow-Orange 14A. Quantity: Scant.

Pistil:
*Number*.—Average: 150 to 200.
*Length*.—0.25 cm.
*Style*.—Length: 0.2 cm. Color: Near RHS Yellow-Green 144B.
*Stigma*.—Shape: Acute. Color: Near RHS Yellow-Green 144C.
*Ovary color*.—Near RHS Yellow-Green 144C.

OTHER CHARACTERISTICS

Seed/fruit: No seeds/fruits detected to date

Temperature tolerance: Plants of the new *Anemone* are hardy to at least USDA Zone 6.

Diseases and pests: Neither resistance nor susceptibility to normal diseases and pests of the new *Anemone* has been observed.

What is claimed is:

1. A new and distinct cultivar of *Anemone* plant named 'FP007' as herein illustrated and described.

* * * * *